United States Patent

Yokoyama et al.

Patent Number: 5,184,895
Date of Patent: Feb. 9, 1993

[54] OPTICAL SENSOR AND THERMAL SENSOR

[75] Inventors: Masaaki Yokoyama, Toyonaka; Mikio Kakui, Minoo, both of Japan

[73] Assignee: MITA Industrial Co., Ltd., Osaka, Japan

[21] Appl. No.: 754,536

[22] Filed: Sep. 4, 1991

[30] Foreign Application Priority Data

Sep. 10, 1990 [JP] Japan .................. 2-240338

[51] Int. Cl.⁵ .......................... G01K 11/16
[52] U.S. Cl. .................. 374/162; 428/913; 430/330
[58] Field of Search ............ 374/17, 19, 141, 159, 374/160, 161, 162; 430/14, 59, 272, 321, 330, 945; 428/913

[56] References Cited

U.S. PATENT DOCUMENTS

| | | | |
|---|---|---|---|
| 3,951,658 | 4/1976 | Marsh et al. | |
| 4,254,209 | 3/1981 | Abe et al. | 430/272 |
| 4,474,865 | 10/1984 | Ong et al. | 430/59 X |
| 4,656,118 | 4/1987 | Ohara et al. | 430/272 |
| 4,956,649 | 9/1990 | Sakai et al. | 428/913 X |
| 5,030,533 | 7/1991 | Bluhm et al. | 430/59 |
| 5,034,296 | 7/1991 | Ong et al. | 430/59 |
| 5,061,536 | 10/1991 | Satake et al. | 428/913 X |

OTHER PUBLICATIONS

Derwent World Patent Index Accession No. 80-491 98C.
Derwent World Patent Index Accession No. 90-250 959.

Primary Examiner—William A. Cuchlinski, Jr.
Assistant Examiner—G. Bradley Bennett
Attorney, Agent, or Firm—Beveridge, DeGrandi & Weilacher

[57] ABSTRACT

An optical sensor has a photosensitive portion which has a first layer including oxo metallic phthalocyanine pigment and a second layer consisting of organic polysilane and shows a sensing of light with a change of color. The optical sensor can also be used as a thermal sensor.

23 Claims, 9 Drawing Sheets

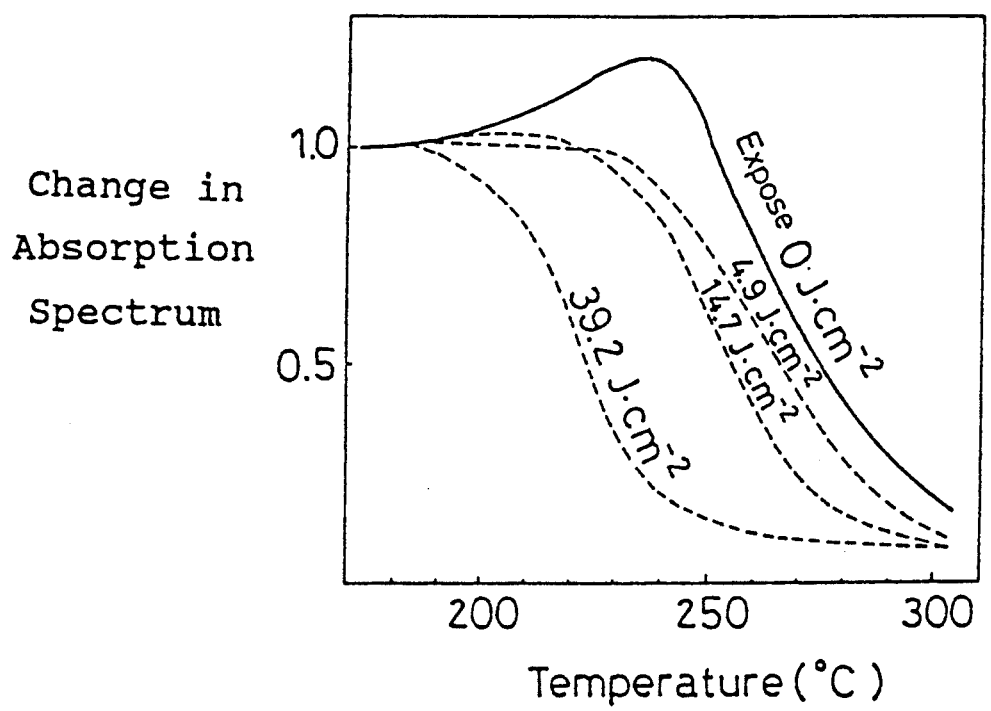

OPTICAL SENSOR AND THERMAL SENSOR

BACKGROUND OF THE INVENTION

1. Field of the Invention

The present invention relates to an optical sensor and a thermal sensor.

2. Description of the Prior Arts

Many kinds of thermal sensors and optical sensors having a structure where a thermosensitive material and a photosensitive material are applied to the surface of paper, film, etc. have already been put to practical use and are being used. Moreover, there are many types of mediums in the form of thermosensitive paper and photosensitive paper for recording and displaying images such as letters, figures, etc.

However, few of the conventional sensors meet a demand for a sensor having an excellent sensitivity, being easily manufactured and whose characteristic is stably maintained.

SUMMARY OF THE INVENTION

An object of the present invention is to provide a plane-type optical sensor and a thermal sensor having an excellent sensitivity, easily manufactured and whose characteristic is stable, where a combination of new materials and a physical and chemical reaction of these materials by adding light energy and heat energy thereto are utilized.

A thermal sensor according to the present invention is characterized in comprising a thermosensitive portion or a photosensitive portion (hereinafter referred to as lamination layer portion) composed of a first layer including oxo metallic phthalocyanine pigment and a second layer consisting of organic polysilane and showing a sensing of heat or light with a change of color.

BRIEF DESCRIPTION OF THE DRAWINGS

This and other objects and features of this invention will become clear from the following description taken in conjunction with the preferred embodiments with reference to the accompanied drawings in which:

FIG. 4 is a graph showing a change in the light absorbance of a (PhMeSi)x/TiO-Pc lamination layer film which is an embodiment by a heating, where a quantity of ultraviolet ray irradiation is the parameter;

DETAILED DESCRIPTION OF THE PREFERRED EMBODIMENT

Figure 3A:
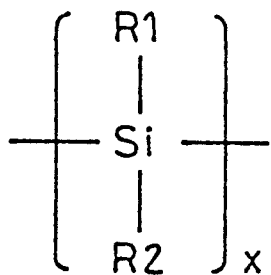
FIGS. 3A and 3B respectively show the chemical formula of organic polysilane and that of oxo metallic phthalocyanine pigment.
Figure 3B:
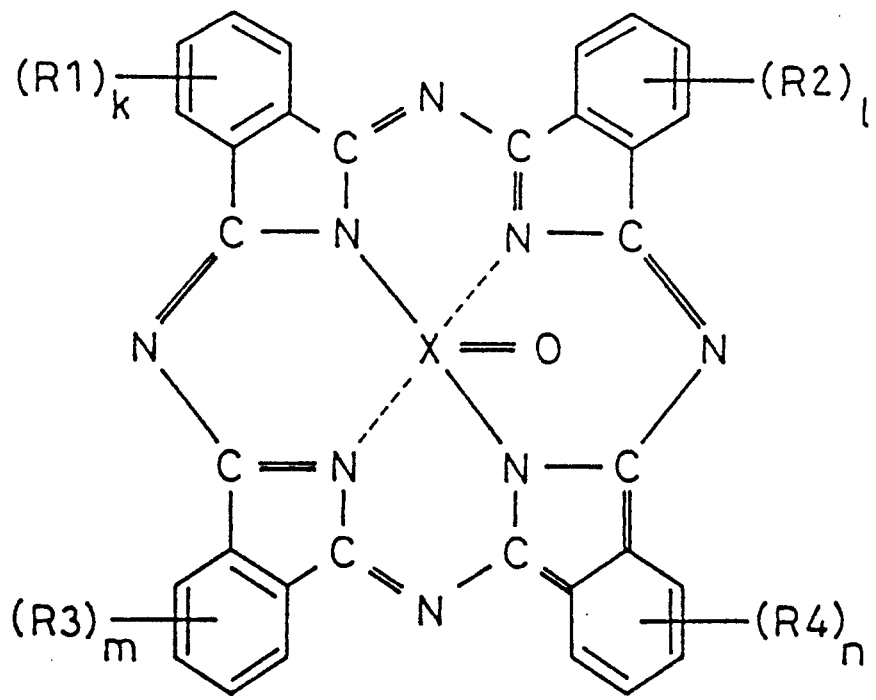

FIGS. 3A and 3B respectively show the chemical formulae of organic polysilane oxo metallic phthalocyanine pigment which constitute a lamination portion of a sensor according to the present invention. In FIG. 3A, in general, R1 and R2 represent lower alkyl, aryl, alkoxy, and acyl radicals, etc. In FIG. 3B, in general, X represents a metallic atom; R1, R2, R3, and R4 represent substituents of hydrogen atoms, halogen atoms, alkyl radicals, alkoxy radicals, aryl radicals, aryloxy radicals, nitro radicals, cyano radicals, hydroxyl radicals, benzyloxy radicals, amino radicals, etc; and k, l, m and n represent integers from 0 to 4.

By heating the lamination layer portion to a temperature equal to or higher than the pyrolyzing point of organic polysilane, the organic polysilane of the second layer is decomposed. Since the pyrolyzing point of organic polysilane is higher than its glass transition point, the second and first layers mix by the above heating, which enables a contact of the above-described decomposition product of organic polysilane and oxo metallic phthalocyanine pigment. Thereby, the decomposition product of organic polysilane reacts on oxo metallic phthalocyanine pigment to decolor the oxo metallic phthalocyanine pigment. Therefore, a thermal sensor having the above-described type of lamination layer portion can be used as a sensor for detecting whether or not the temperature has risen to a temperature equal to or higher than the pyrolyzing point of organic polysilane.

Next, when ultraviolet ray is irradiated on the above lamination layer portion, organic polysilane of the second layer is decomposed (photon decomposition) by the light energy of the ultraviolet ray. At this point of time, however, the decomposition product remains in the second layer, so that nothing is changed externally. Thereafter, by heating the lamination layer portion on which ultraviolet ray is irradiated to a temperature equal to or higher than the glass transition point of organic polysilane, similarly to the above-described case, the second and first layers mix, so that the decoloring reaction of oxo metallic phthalocyanine pigment is caused by a contact of organic polysilane with the oxo metallic phthalocyanine pigment. Therefore, an optical sensor having the above-described type of lamination layer portion can be used as a sensor for detecting whether or not ultraviolet rays have been irradiated.

Figure 1A:
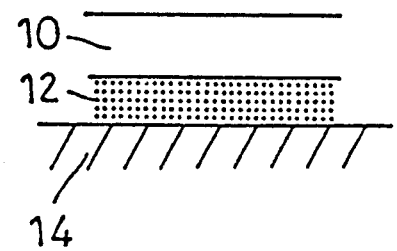
FIGS. 1A to 1C are views showing a process for making a recording onto an image recording medium according to the present invention.
Figure 1B:
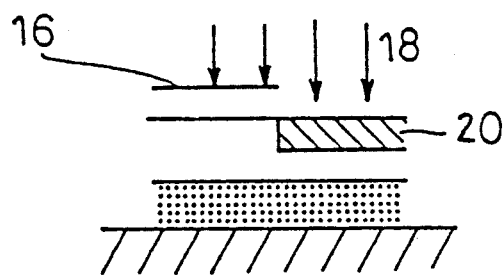
Figure 1C:
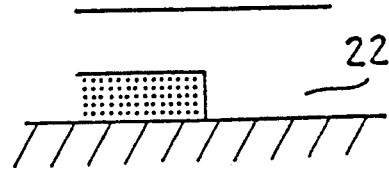

As described above, in the lamination layer portion according to the present invention, the decoloring of oxo metallic phthalocyanine pigment is caused by two kinds of processes (heating to a temperature equal to or higher than the pyrolyzing point of organic polysilane, and irradiating with ultraviolet rays plus heating to a temperature equal to or higher than the glass transition point). Therefore, by conducting the above-described processes, that is, the heating or the irradiating ultraviolet rays plus heating, selectively on the lamination layer portion, the laminated portion can be used as an image recording medium. The following is a more detailed description of the image recording method:

i) As shown in FIG. 1A, by selectively heating according to a pattern representing an image to be recorded a recording portion consisting of an oxo metallic phthalocyanine pigment layer 12 (which may include binder polymer), applied to a base layer 14 made of paper, film, etc., and of an organic polysilane layer 10, the heated portion is decolored to display the image. For the selective heating, a laser beam and thermal head can be used.

ii) The recording portion shown in FIG. 1A is covered with a mask 16 formed in accordance with an image to be recorded, and ultraviolet ray 18 is irradiated thereon (FIG. 1B). On a portion 20 of the organic polysilane 10 where the ultraviolet ray 18 is irradiated, the photon decomposition of organic polysilane is caused. This decomposition cannot be viewed by the eye, and the image is recorded as a latent image. Then, by heating the entire surface of the recording portion to a temperature equal to or higher than the glass transition point of organic polysilane, both of the layers mix, so that the oxo metallic phthalocyanine pigment is decolored only in a portion 22 where there is the organic polysilane decomposed by the irradiation of ultraviolet ray (FIG. 1C).

iii) In the above-described method ii), an image is recorded by a selective irradiation of ultraviolet rays. An image can also be recorded by irradiating ultraviolet on the entire surface and thereafter, heating it selectively according to the image.

When binder polymer is used for the first layer 12, it is required that the heating after the irradiation of ultraviolet ray is to a temperature equal to or higher than the glass transition point of the binder polymer.

Figure 2A:
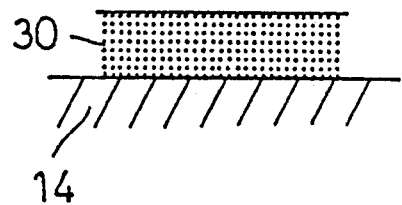
FIGS. 2A to 2C are views showing a process for making an image recording onto a dispersion-type recording layer.
Figure 2B:
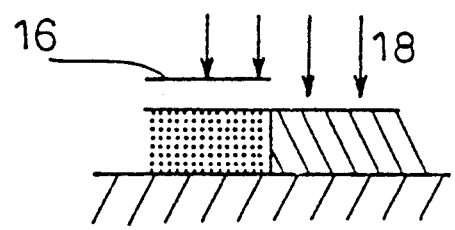
Figure 2C:
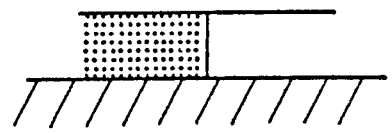

Moreover, when a dispersion-type recording layer 30 (where oxo metallic phthalocyanine pigment is dispersed in organic polysilane) is formed on the base layer 14 by mixing organic polysilane and oxo metallic phthalocyanine pigment as shown in FIGS. 2A to 2C, the recording layer can also record images with high contrast as an image recording medium in the same manner as that shown in FIG. 1B. This is because even if ultraviolet rays are irradiated, there is no sufficient chance for organic polysilane and oxo metallic phthalocyanine pigment to contact with each other unless the recording layer is heated, so that a satisfactory decoloring reaction is not caused. Therefore, this dispersion-type structure can also be used as an optical sensor and a thermal sensor in the same manner as that of the above-described lamination-layer-type structure.

A more detailed description of the embodiment of the present invention will hereinafter be given with reference to the drawings.

Formation of a Lamination Layer Film

Firstly, phenylmethylpolysilane (PhMeSi)x was produced as an embodiment of the organic polysilane. The following is the method. Under the existence of 13 g metallic sodium, 50 g phenylmethyldichlorosilane (0.28 mol) was heated to 135° C. in 200 ml dry toluene, and was reacted for approximately 11 hours while being agitated. After a cooling, ethanol was added to the solution where dark violet precipitation had been deposited to make the sodium which had not reacted into ethoxide. After the precipitation was filtered out, the solution was dried, and was dissolved in toluene. The solution was dropped into ethanol and re-precipitated to obtain phenylmethylpolysilane. The yield of the phenylmethylpolysilane was 10.2 g and 34%. In FIG. 3A showing the phenylmethylpolysilane, R1 represents the phenyl radical and R2 represents the methyl radical.

Next, titanylphthalocyanine TiO-Pc (shown in FIG. 3B) as an example of the oxo metallic phthalocyanine pigment where Ti is a metal X. The titanylphthalocyanine used was $\alpha$ type manufactured by Sanyo Shikiso Co., Ltd. The lamination layer film consisting of the $\alpha$ type and phenylmethylpolysilane was produced as hereinafter described. Ninety-mg titanylphthalocyanine was added to 6 ml tetrahydrofuran (THF). After kneading for a whole day and night in a ball mill, it was dispersed. Ninety-mg polyvinyl butyral (S-LEC BM-2 manufactured by Sekisui Chemical Co., Ltd. was used) was added thereto, and it was dispersed in a ball mill for one more hour to be made into coating liquid. This was spin-coated on a transparent glass substrate (silica glass or slide glass) to form a titanylphthalocyanine dispersion film. Next, 35 mg phenylmethylpolysilane was dissolved in 0.35 ml benzene, and it was spin-coated on the titanylphthalocyanine dispersion film to form a (PhMeSi)x/TiO-Pc lamination layer film. In both of the titanylphthalocyanine dispersion film and the phenylmethylpolysilane film, uniform layers were extremely easily obtained by the spin-coating.

Optical and Thermal Characteristics of the Lamination Layer Film

FIG. 4 shows a change in absorbance, to a 690 nm red light, of the (PhMeSi)x/Tio-Pc lamination layer film formed as described above when the lamination layer film was heated to 300° C. after ultraviolet rays having intensities of 0 to 39.2 J/cm$^2$ were irradiated at room temperature. FIG. 4 also shows the change in absorption spectrum when ultraviolet rays having an intensity of 4.9 and 14.7 J/cm$^2$ are used for irradiation. From the figure, it is understood that, for example, when the lamination layer film is heated to approximately 240° C., there is a large difference in absorbance between the portion where ultraviolet ray is irradiated (39.2 J/cm$^2$) and the portion where ultraviolet ray is not irradiated (0 J/cm$^2$).

This indicates that this lamination layer film can be used for an optical sensor for ultraviolet rays. That is, the optical sensor is placed at a place where ultraviolet rays are to be detected, and by heating the sensor to approximately 240° C. thereafter, whether or not ultraviolet rays are irradiated is detected by an extremely clear change of color (that is, the difference in absorbance). Moreover, by irradiating ultraviolet rays in accordance with an image and heating the sensor thereafter, a high-contrast, clear image can be recorded.

Further, by previously irradiating ultraviolet rays on a part of the lamination layer and leaving it at a place where temperature rises, the lamination layer can be used as a thermal sensor for detecting whether or not the temperature at the place has risen to a range between 200° C. to 300° C. The lamination layer film can also be used for a thermal sensor which can finely detect temperature by previously irradiating a different quantity of ultraviolet ray on each portion of the lamination layer film, respectively.

FIG. 4 also shows that by heating the lamination layer film to a temperature equal to or more than approximately 300° C., the absorbance is decreased (that is, decoloring is caused) even if ultraviolet rays are not previously irradiated, which indicates that the lamination layer film can also be used as a thermal sensor and an image recording medium.

Principle of the Decoloring

Figure 5:
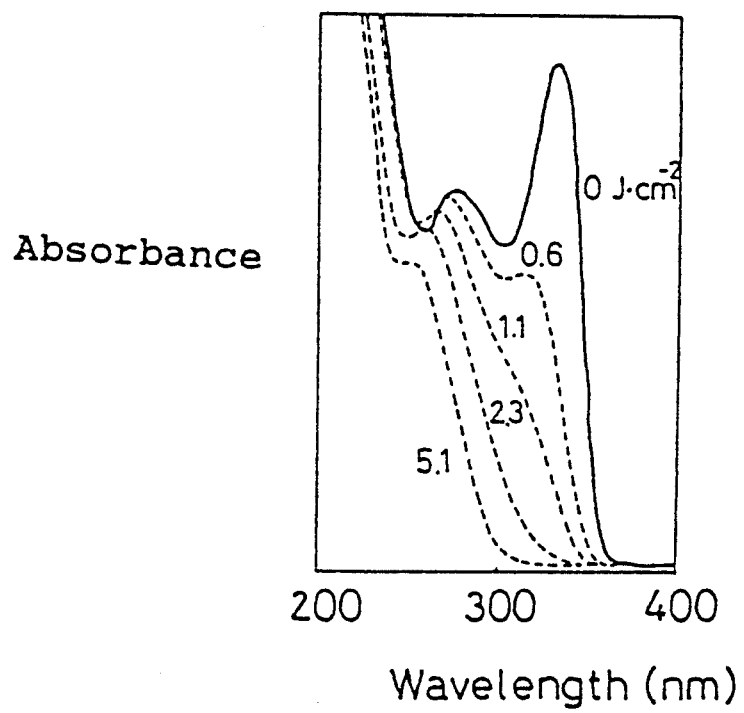
FIG. 5 is a graph showing a absorption spectrum of the (PhMeSi)x/Tio-Pc lamination layer film after ultraviolet ray irradiation, where a quantity of ultraviolet ray irradiation is the parameter.
Figure 6:
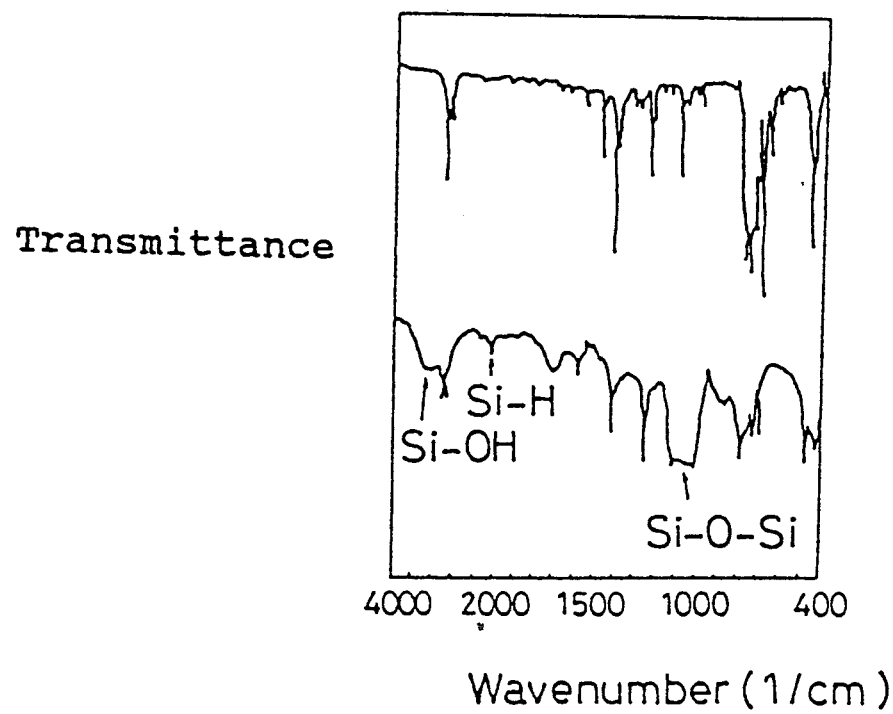
FIG. 6 is a graph showing a result of an FT-IR measurement of phenylmethylpolysilane which is an embodiment before (the upper) and after (the lower) ultraviolet ray irradiation.

In order to search the cause of such optical and thermal characteristics of the (PhMeSi)x/Tio-Pc lamination layer film, firstly, the decomposition of phenylmethylpolysilane by the irradiation of ultraviolet rays was examined. After 300 nm to 400 nm ultraviolet rays having intensities of 0 J/cm$^2$ to 5.1 J/cm$^2$, respectively, were irradiated to a simple component film of phenylmethylpolysilane, the absorbance of the film to 200 nm to 400 nm ultraviolet rays was measured. FIG. 5 shows the result. FIG. 5 shows the absorbance for 0, 0.6, 1.1, 2.3 and 5.1 J/cm$^2$ intensity ultraviolet rays. A peak of $\lambda_{MAX}=331$ nm which appears when ultraviolet rays are not irradiated (0 J/cm$^2$) rapidly disappears after ultraviolet rays are irradiated. Since the peak of $\lambda_{MAX}=331$ nm corresponds to an Si-Si compound which is the principal chain of phenylmethylpolysilane, it is understood that the Si-Si compound which is the principal chain is cut off by the irradiation of ultraviolet ray. Moreover, FIG. 6 shows an FT-IR spectrum of phenylmethylpolysilane measured before and after the irradiation of ultraviolet rays (the upper is before the irradiation, and the lower is after the irradiation), where the existence of Si-OH compound and Si-O-Si compound is confirmed. From the above, it is understood that by irradiating ultraviolet rays on phenylmethylpolysilane, the Si-Si compound which is the principal chain is cut off to form a polymer having a bond in siloxane.

The formation of the siloxane chain (Si-O-Si) which is a loose compound by the decomposition of phenylmethylpolysilane shows that the phenomenon that the degree of freedom of polymer movement at the ultraviolet-ray-irradiated portion is improved (that is, a glass transition point Tg is decreased) is one of the causes of a shift (see FIG. 4) of the decoloring reaction toward a low temperature side.

Figure 7:
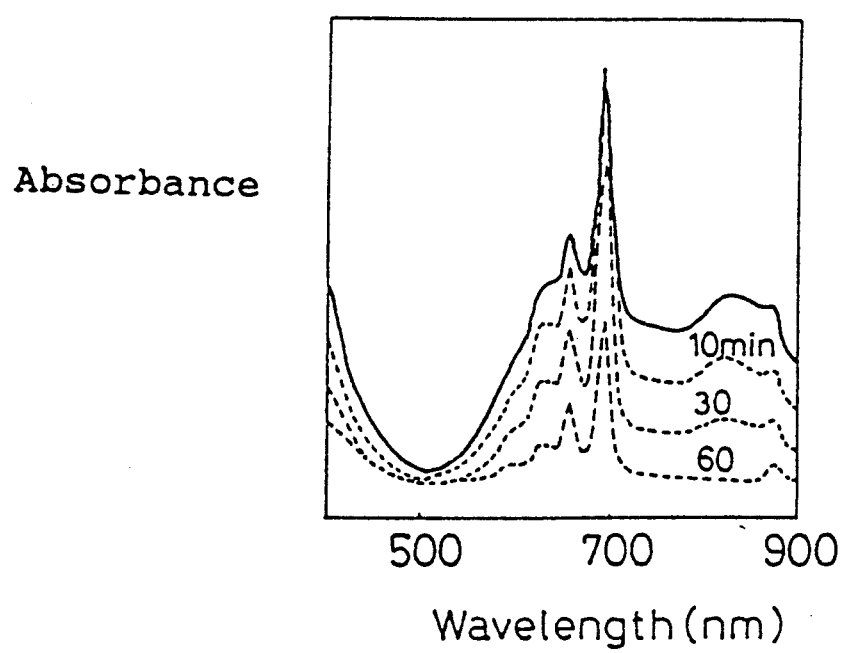
FIG. 7 is a graph showing a change in the absorption spectrum when ultraviolet ray is irradiated on a solution where titanylphthalocyanine is dispersed in a toluene solution of phenylmethylpolysilane.

Next, in order to examine the decoloring reaction of titanylphthalocyanine TiO-Pc, an examination was made with a dispersion solution of titanylphthalocyanine. Titanylphthalocyanine was dispersed in a toluene solution of phenylmethylpolysilane, and after ultraviolet rays were irradiated thereon for 0 to 60 minutes, the absorption spectra of the solution were measured. FIG. 7 shows the result. FIG. 7 shows the change in absorbance spectra after 10, 30 and 60 minutes. It is understood that in a dispersion solution where a free contact of phenylmethylpolysilane and titanylphthalocyanine is possible, the decoloring reaction is caused only by the irradiation of ultraviolet rays.

Figure 8:
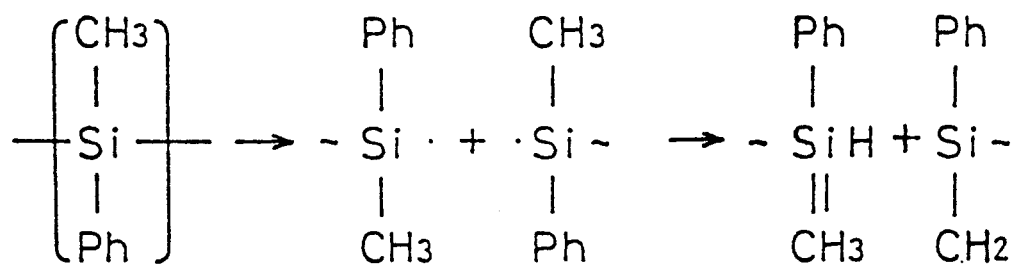
FIG. 8 shows the chemical formulae showing a process of decomposition of phenylmethylpolysilane by photon or heat.

As a result of the above research, it is considered that the decoloring phenomenon of the (PhMeSi)x/TiO-Pc lamination layer film is caused in the following process. Firstly, by the irradiation of ultraviolet rays, the Si-Si compound of phenylmethylpolysilane is cut off as shown in FIG. 8, so that decomposition products such as silyl radical, siloxane compound, Si-H compound, etc. are produced. When the temperature is not high, however, the decoloring reaction of titanylphthalocyanine pigment is not caused, since these decomposition products cannot move from the phenylmethylpolysilane layer to the titanylphthalocyanine layer. When the lamination layer film is heated to a temperature equal to or higher than the glass transition point temperature Tg of phenylmethylpolysilane, phenylmethylpolysilane having the silyl radical and siloxane compound moves to the titanylphthalocyanine layer, and decomposes a phthalocyanine ring to decolor the titanylphthalocyanine pigment.

Figure 9:
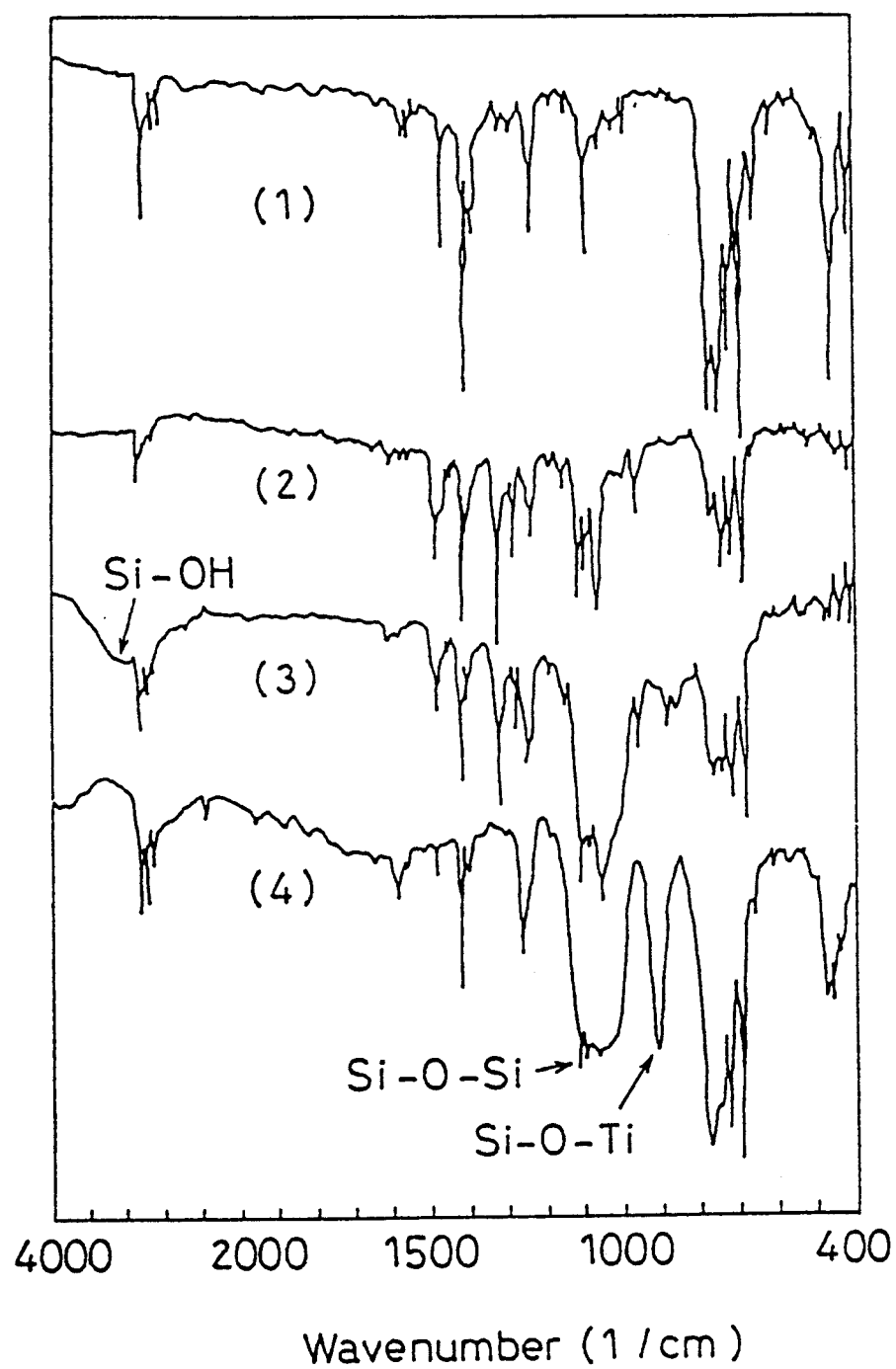
FIG. 9 is a graph showing a result of an FT-IR measurement of each of (1) only phyenylmethylpolysilane (PhMeSi)x, (2) the (PhMeSi)x/TiO-Pc lamination layer film, (3) after ultraviolet ray is irradiated on the (PhMeSi)x/TiO-Pc lamination layer film for two hours, and (4) after the lamination layer film is heated at 250° C. and decolored.

FIG. 9 shows the result of the FT-IR measurement in each of the following conditions: (1) only phenylmethylpolysilane (PhMeSi)x; (2) the (PhMeSi)x/TiO-Pc lamination layer film; (3) after ultraviolet rays are irradiated on the (PhMeSi)x/TiO-Pc lamination layer film for two hours; and (4) after, further to the condition (3), the lamination layer film is heated at 250° C. and decolored. By comparing (1) and (2), it is confirmed that absorption peaks 1330, 1280, 1120, 1060 and 890 cm$^{-1}$ shown by a mark ○ in (2) are those of titanylphthalocyanine pigment. These peaks still remain after the irradiation with ultraviolet rays (3), although it is hidden in a large absorption band of 1000 to 1100 cm$^{-1}$ showing the formation of the Si-O-Si compound by the photon oxidation of the organic polysilane. After the heating (4), however, these peaks shown by the mark ○ disappear, and instead, the peak (approximately 920 cm$^{-1}$) of Si-O-Ti compound that is speculated to be a reaction product of Si-OH compound, which is a decomposition product of phenylmethylpolysilane after the irradiation of ultraviolet rays (3) and titanylphthalocyanine pigment, is generated.

As described above, by this embodiment, it has been clarified that by heating the (PhMeSi)x/TiO-Pc lamination layer film to an appropriate temperature after the irradiation of ultraviolet rays, images can be recorded with extremely high contrast. Moreover, as its mechanism, it was clarified that the Si-Si principal chain of the organic polysilane is decomposed by the previous ultraviolet ray irradiation, and active species such as silyl radical, etc. which is the decomposition product thereof reacts on the oxo metallic phthalocyanine pigment to decolor the oxo metallic phthalocyanine pigment.

FIG. 4 further shows that even after a large amount of ultraviolet ray (39.2 J/cm$^2$) is irradiated, the decolorin does not occur until the temperature reaches 200° C. Therefore, the recording portion where an image is once recorded is extremely stable in a normal condition (at room temperature), so that a high contrast at the time of the recording is maintained for a long period of time. The image recording medium before the recording, optical sensor and thermal sensor also have the characteristic of high stability.

Figure 10:
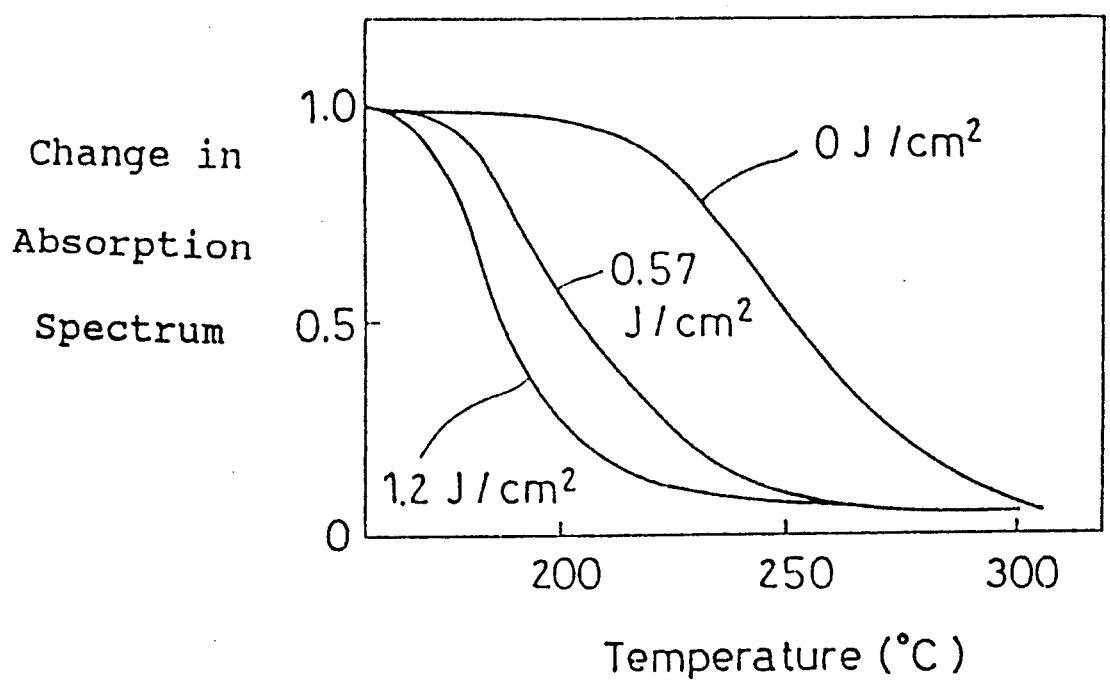
FIG. 10 is a graph showing a change in the light absorbance, by heating of the (PhMeSi)x/TiO-Pc lamination layer film when a first layer is an evaporation film of the simple body of oxo metallic phthalocyanine pigment, where a quantity of ultraviolet ray is the parameter.

In the above-described embodiment, a mixture of oxo metallic phthalocyanine pigment with a binder (phenylmethylpolysilane) whose glass transition point is relatively low was used as the first layer of the lamination layer film. FIG. 10 is a graph showing a change (the conditions are the same as those in FIG. 4 of the above-described embodiment) in the light absorbance according to the heating temperature when the first layer of the lamination film is an evaporation layer consisting of only oxo metallic phthalocyanine pigment and the second layer consists of phenylmethylpolysilane, where a quantity of ultraviolet irradiation is the parameter. FIG. 10 shows the change in absorption as a function of temperature for ultraviolet radiation having the following intensities: 0, 0.57 and 1.2 J/cm². The relation nearly the same as that shown in FIG. 4 is obtained, from which it is understood that quantitatively, the above-described examination applies to this case. The temperature at which the light absorbance decreases, however, is closer to the low temperature side compared with the case shown in FIG. 4, so that the decoloring reaction is caused at a lower temperature.

In the above description, only the lamination layer structure was described. From the results of the above-described various experiments, however, it is clear that when a dispersion-type monolayer is formed by mixing the organic polysilane and the oxo metallic phthalocyanine pigment, the monolayer can be used as an optical sensor, a thermal sensor and an image recording medium similar to the above-described embodiment of the lamination layer construction.

As described above, the present invention as an optical sensor can be used as a monitor sensor by affixing it on a poriton where ultraviolet rays are not to be irradiated, and also can detect whether or not a predetermined amount of ultraviolet ray has correctly been irradiated by affixing it on a portion where ultraviolet rays are to be irradiated. Further, if the temperature in the heating thereafter is uniform, since the discoloring degree of oxo metallic phthalocyanine pigment is varied according to a quantity of ultraviolet irradiation, an approximate quantity of ultraviolet irradiation can be judged.

As a thermal sensor, by affixing a thermal sensor according to the present invention on a poriton, e.g. a bearing portion, etc. of a rotating machine, where it is dangerous if the operation temperature exceeds a predetermined temperature (or by applying the thermosensitive portion of the lamination layer structure directly to the portion), a dangerous condition can be detected at a glance. Furthermore, since the thermal sensor according to the present invention does not return to its original condition if once decolored by being heated to a temperature equal to or higher than a predetermined temperature, a dangerous portion can be found even after an operation of the machine is finished. Moreover, since the degree of the decoloring is varied according to the temperature to which the sensor is heated, approximately how many degrees of temperature the sensor has been heated to can be found by comparing with a predetermined color standard.

As an image recording medium, the present invention can be used as a medium which does not become easily decolored as long as maintained at room temperature in a normal condition and where displays do no disappear.

In any of the above-described cases, the present invention, where a change in the light absorbance of the pigment by light and heat is extremely large, serves as a clear optical sensor and a clear thermal sensor and as a high-contrast, clear recording medium. All of the materials used for the present invention are organic materials, whereby the lamination layer film can easily by produced. Further, since it is stable chemically and thermally at an ordinary temperature, the lamination layer film can be maintained for a long period of time, no deteriorating of characteristics as an optical and thermal sensor being caused. As an image recording medium, there being no possibility for recorded images to disappear, the present invention can be used as a stable recording medium.

Obviously, many modifications and variations of the present invention are possible in light of the above teachings. It is therefore to be understood that within the scope of the appended claims, the invention may be practiced other than as specifically described.

What is claimed is:

1. An optical sensor whose photosensitive portion comprises a first layer including an oxo metallic phthalocyanine pigment and a second layer consisting of organic polysilane, said optical sensor indicating sensing of light by a decoloring reaction of said oxo metallic phthalocyanine pigment and said organic polysilane.

2. An optical sensor as claimed in claim 1, wherein in said photosensitive portion, an absorbance for red light differs between a portion where light is irradiated and a portion where light is not irradiated when heated after light is irradiated.

3. An optical sensor as claimed in claim 1, wherein in said photosensitive portion, the organic polysilane in said second layer is decomposed by light energy at a portion where ultraviolet rays are irradiated when ultraviolet rays are irradiated, and thereafter, the decomposed organic polysilane and the oxo metallic phthalocyanine pigment in the first layer react when heated to a temperature equal to or higher than a glass transition point to decolor the oxo metallic phthalocyanine pigment at the portion where ultraviolet rays are irradiated.

4. A thermal sensor whose thermosensitive portion comprises a first layer including an oxo metallic phthalocyanine pigment and a second layer consisting of organic polysilane, said thermal sensor indicating sensing of heat by a decoloring reaction of said oxo metallic phthalocyanine pigment and said organic polysilane.

5. A thermal sensor as claimed in claim 4, wherein a temperature can be finely detected by previously irradiating a different quantity of ultraviolet ray on different portions of said thermosensitive portion.

6. An optical sensor according to claim 1, wherein said organic polysilane is of the formula:

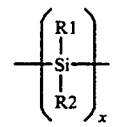

wherein R1 and R2 represent a lower alkyl radical, an aryl radical, an alkoxy radical, and acyl radical.

7. An optical sensor according to claim 1, wherein said organic polysilane is phenylmethylpolysilane.

8. An optical sensor according to claim 1, wherein said oxo metallic phthalocyanine pigment is of the formula:

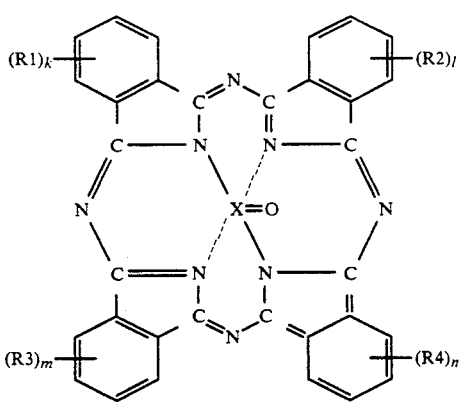

wherein:

X represents a metallic atom;

R1, R2, R3 and R4 represent substituents of a hydrogen atom, a halogen atom, an alkyl radical, an alkoxy radical, an aryl radical, an aryloxy radical, a nitro radical, a cyano radical, a hydroxyl radical, a benzyloxy radical and an amino radical; and k, l, m and n are integers from 0 to 4.

9. An optical sensor according to claim 1, wherein said oxo metallic phthalocyanine pigment is titanylphthalocyanine.

10. An optical sensor whose photosensitive portion comprises a single dispersion layer prepared by mixing an oxo metallic phthalocyanine pigment and organic polysilane, said optical sensor indicating sensing of light by a decoloring reaction of said oxo metallic phthalocyanine pigment and said organic polysilane.

11. An optical sensor according to claim 10, wherein said organic polysilane is of the formula:

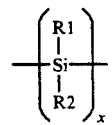

wherein R1 and R2 represent a lower alkyl radical, an aryl radical, an alkoxy radical, and acyl radical.

12. An optical sensor according to claim 10, wherein said organic polysilane is phenylmethylpolysilane.

13. An optical sensor according to claim 10, wherein said oxo metallic phthalocyanine pigment is of the formula:

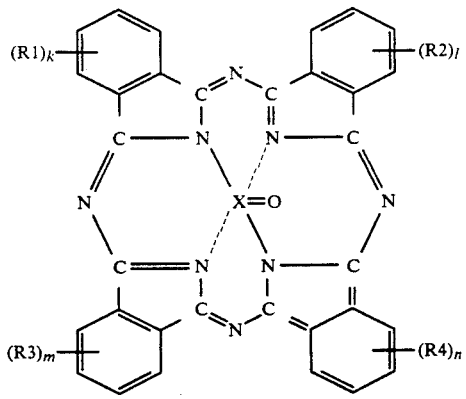

wherein:

X represents a metallic atom;

R1, R2, R3 and R4 represent substituents of a hydrogen atom, a halogen atom, an alkyl radical, an alkoxy radical, an aryl radical, an aryloxy radical, a nitro radical, a cyano radical, a hydroxyl radical, a benzyloxy radical and an amino radical; and k, l, m and n are integers from 0 to 4.

14. An optical sensor according to claim 10, wherein said oxo metallic phthalocyanine pigment is titanylphthalocyanine.

15. A thermal sensor according to claim 4, wherein said organic polysilane is of the formula:

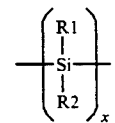

wherein R1 and R2 represent a lower alkyl radical, an aryl radical, an alkoxy radical, and acyl radical.

16. A thermal sensor according to claim 4, wherein said organic polysilane is phenylmethylpolysilane.

17. A thermal sensor according to claim 4, wherein said oxo metallic phthalocyanine pigment is of the formula:

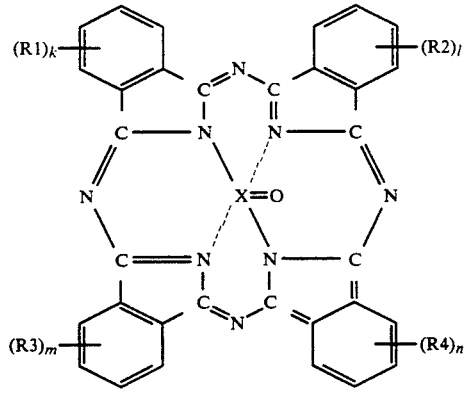

wherein:

X represents a metallic atom;

R1, R2, R3 and R4 represent substituents of a hydrogen atom, a halogen atom, an alkyl radical, an alkoxy radical, an aryl radical, an aryloxy radical, a nitro radical, a cyano radical, a hydroxyl radical, a benzyloxy radical and an amino radical; and k, l, m and n are integers from 0 to 4.

18. A thermal sensor according to claim 4, wherein said oxo metallic phthalocyanine pigment is titanylphthalocyanine.

19. A thermal sensor whose thermosensitive portion comprises a single dispersion layer prepared by mixing an oxo metallic phthalocyanine pigment and organic polysilane, said thermal sensor indicating sensing of heat by a decoloring reaction of said oxo metallic phthalocyanine pigment and said organic polysilane.

20. A thermal sensor according to claim 19, wherein said organic polysilane is of the formula:

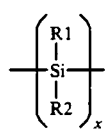

wherein R1 and R2 represent a lower alkyl radical, an aryl radical, an alkoxy radical, and acyl radical.

21. A thermal sensor according to claim 19, wherein said organic polysilane is phenylmethylpolysilane.

22. A thermal sensor according to claim 19, wherein said oxo metallic phthalocyanine pigment is of the formula:

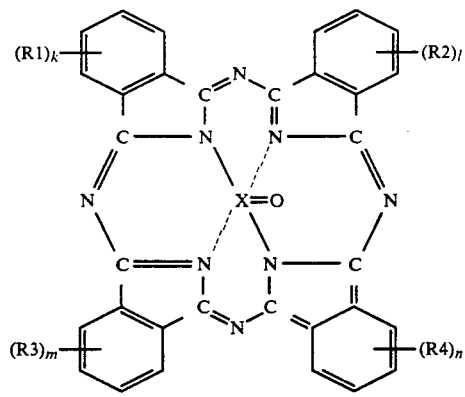

wherein:

X represents a metallic atom;

R1, R2, R3 and R4 represent substituents of a hydrogen atom, a halogen atom, an alkyl radical, an alkoxy radical, an aryl radical, an aryloxy radical, a nitro radical, a cyano radical, a hydroxyl radical, a benzyloxy radical and an amino radical; and k, l, m and n are integers from 0 to 4.

23. A thermal sensor according to claim 19, wherein said oxo metallic phthalocyanine pigment is titanylphthalocyanine.

* * * * *